US00PP10678P

United States Patent [19]

Griffith

[11] Patent Number: Plant 10,678

[45] Date of Patent: Nov. 10, 1998

[54] *ILEX GLABRA* PLANT NAMED 'GREEN BILLOW'

[75] Inventor: Mark P. Griffith, Watkinsville, Ga.

[73] Assignee: Griffith Propagation Nursery, Watkinsville, Ga.

[21] Appl. No.: 874,437

[22] Filed: Jun. 16, 1997

[51] Int. Cl.[6] ..... A01H 5/00

[52] U.S. Cl. ..... Plt./65

[58] Field of Search ..... Plt./65

*Primary Examiner*—James R. Feyrer
*Assistant Examiner*—Kent L. Bell
*Attorney, Agent, or Firm*—C. A. Whealy

[57] ABSTRACT

A distinctive cultivar of Inkberry, *Ilex glabra*, plant named 'Green Billow', characterized by its compact, mounded, broadly-spreading habit; branches that are finely-textured due to very freely and horizontal branching and closely-spaced leaves which produce a dense, and not open, plant habit; good retention of lower foliage; small, glossy dark green summer foliage and burnished grayed-purple winter foliage; small cream-white flowers that form blackish drupes; and wide adaptability, suitable for wet and moist soils and hardiness zones 4 to 9.

3 Drawing Sheets

The present invention relates to a new and distinct cultivar of Inkberry plant, botanically known as *Ilex glabra* (L.) A. Gray, and hereinafter referred to by the cultivar name 'Green Billow'.

Inkberry is the most widely distributed evergreen holly in North America. Inkberry occurs from Nova Scotia to Florida and west to the Gulf Coast of Texas. This species has widespread adaptability, zones 4 to 9, and is typically found in moist to wet soil areas. The limited use of Inkberry in the landscape is due to variability in plant size and growth habit and loss of lower leaves. Of the more than twenty cultivars of Inkberry that have been described, the cultivars 'Compacta', 'Nordic', 'Densa', and 'Shamrock' are considered to be the most compact. However these cultivars become tall (usually taller than 150 cm) and leggy and usually loose the lower 20 to 30 percent of their leaves. There is a need for compact (less than 90 cm), densely-branched, foliage-retaining *Ilex glabra* cultivars that will substitute for the widely used but less adaptable *Ilex crenata* 'Helleri' and other Japanese hollies.

The new cultivar was discovered by the inventor in Watkinsville, Ga., as a branch sport of the nonpatented *Ilex glabra* cultivar 'Niagra', and was observed in a group of plants of the parent cultivar in March, 1995.

Asexual reproduction of the new cultivar by cuttings in Watkinsville, Ga., has shown that the unique features of this new Inkberry are stable and are reproduced true to type in successive propagations.

The new cultivar has not been observed under all possible environmental conditions. The phenotype may vary significantly with variations in environment such as temperature and light and fertility levels, without, however, any variance in genotype.

The following traits have been repeatedly observed and are determined to be the unique characteristics of 'Green Billow'.

1. Compact, mounded, broadly-spreading habit. Plants spread horizontally and are usually twice as wide as high, that is, about 45 to 75 cm high and 90 to 150 cm wide.
2. The branches are finely-textured due to very freely and horizontal branching and closely-spaced leaves which produce a dense, and not open, plant habit.
3. Good retention of lower foliage.
4. Small, glossy dark green summer foliage and burnished grayed-purple winter foliage.
5. Small cream-white flowers that form blackish drupes.
6. Very adaptable, suitable for wet and moist soils and hardiness zones 4 to 9.

The following characteristics differentiate the new Inkberry from the parent cultivar 'Nigra' and other Inkberry cultivars commercially known and used in the nursery industry:

1. Plants of the new Inkberry are more compact denser, mounding and horizontally spreading.
2. Plants of the new Inkberry have a more uniform plant shape.
3. Leaves are spaced twice as closely on stems of plants of the new Inkberry compared to plants of the cultivar 'Niagra'.
4. Flowers and fruits of the new Inkberry are approximately one half the size of plants of other cultivars of *Ilex glabra*.

BRIEF DESCRIPTION OF THE PHOTOGRAPHS

The accompanying colored photographs illustrate the overall appearance and foliage color of the new Inkberry, showing the colors as true as it is reasonably possible to obtain in colored reproductions of this type.

The photograph on the first sheet of photographs comprises a top perspective view of a typical plant of the cultivar 'Green Billow'.

The photograph on the second sheet is a close-up view of typical leaves of the cultivar 'Green Billow'.

The photograph on the third sheet are top perspective views of typical plants of the cultivars 'Niagra' (top) and 'Green Billow' (bottom) showing the differences in plant size, growth habit and foliage color. Actual foliage colors may differ from foliage colors in the photographs due to light reflectance.

DETAILED BOTANICAL DESCRIPTION

The following observations, measurements, values and comparisons describe plants grown in Watkinsville, Ga., under commercial practice. In the following description, color references are made to The Royal Horticultural Society Colour Chart except where general terms of ordinary dictionary significance are used.

Botanical classification: *Ilex glabra* (L.) A. Gray cultivar 'Green Billow'.

Parentage: Naturally-occurring branch sport of nonpatented *Ilex glabra* cultivar 'Niagra'.

Propagation:

*Type*.—By cuttings.

Plant description:

*Plant form*.—Compact, mounded and broadly-spreading shrub. Very freely and horizontal branching and closely-spaced leaves produces a dense, and not open, plant habit. Plants uniform in shape.

*Plant size*.—Usually twice as wide as high, that is, about 45 to 75 cm high and 90 to 150 cm wide.

*Stem description*.—Internode length: 3 to mm. Stem texture: Slender, glabrous. Stem color: One and two-year old stems are yellow-green, 145D. Apices are brownish-purple, 200D.

*Foliage description*.—Leaf length: 1.6 to 2 cm. Leaf width: 6 to 11 mm. Leaf shape: Symmetrical, elliptic-oval to elliptic-obovate, with acute apex and cuneate base. Leaf margin: Two to three glandular, mucronate teeth on each margin. Leaf texture: Glabrous, glossy. Leaf color: Summer foliage, abaxial surface: Lustrous dark green, 137A. Summer foliage, adaxial surface: Yellow-green, 146B. Winter foliage: Exposed to sunlight, burnished grayed-purple, 187A. Petiole length: 3 to 5 mm.

Flower description:

*Flower description*.—Number of petals: Six. Diameter: About 6 mm. Color: Cream white.

*Fruit description*.—Type: Drupe. Shape: Globose. Diameter: About 4 mm. Color: Blackish.

Disease resistance: Resistance to known pathogens of Inkberry has not been observed.

It is claimed:

1. A new and distinct Inkberry, *Ilex glabra* plant named 'Green Billow', as illustrated and described.

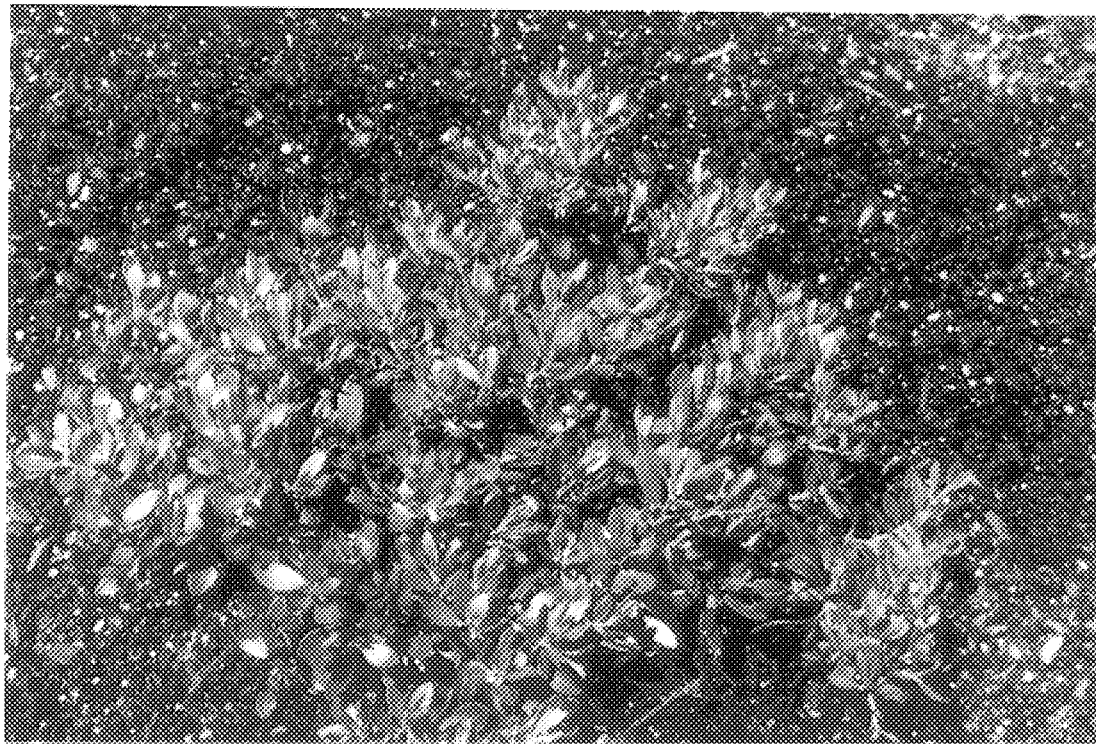

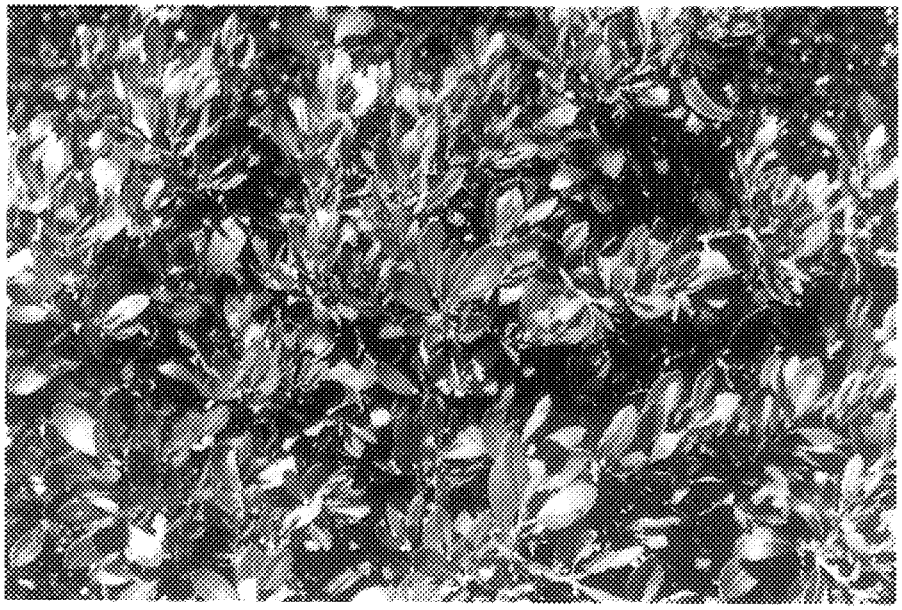

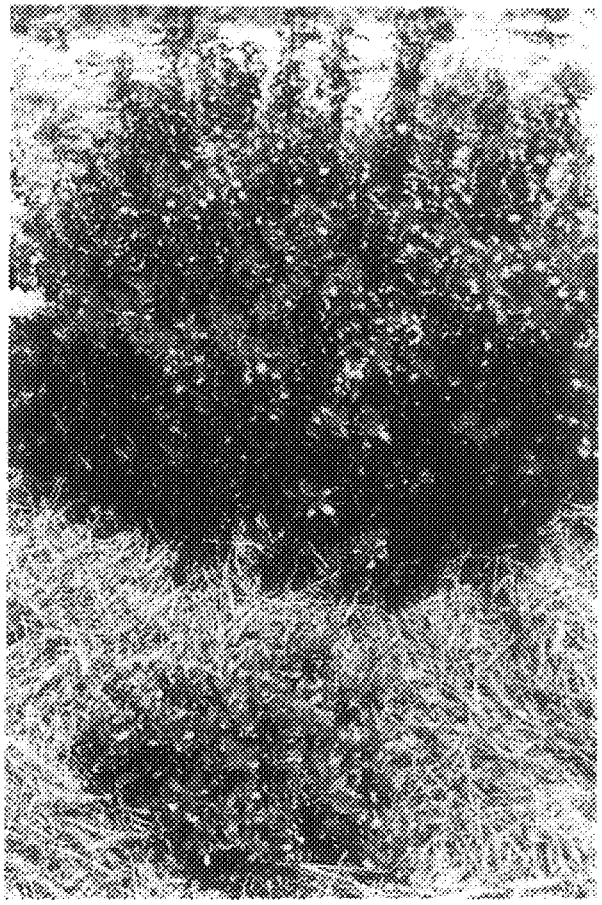

* * * * *